(12) United States Patent
Yanagawa

(10) Patent No.: US 6,589,559 B1
(45) Date of Patent: Jul. 8, 2003

(54) NASALLY ADMINISTRABLE COMPOSITIONS

(75) Inventor: Akira Yanagawa, Yokohama (JP)

(73) Assignee: DOTT Research Laboratory, Yokohama (JP)

( * ) Notice: Subject to any disclaimer, the term of this patent is extended or adjusted under 35 U.S.C. 154(b) by 0 days.

(21) Appl. No.: 09/673,466

(22) PCT Filed: Feb. 16, 2000

(86) PCT No.: PCT/JP00/00864

§ 371 (c)(1),
(2), (4) Date: Oct. 17, 2000

(30) Foreign Application Priority Data

Feb. 22, 1999 (JP) .......................................... 11-043714

(51) Int. Cl.$^7$ ................................................. A61K 9/14
(52) U.S. Cl. ...................... 424/489; 424/435; 424/45; 424/46; 514/2; 514/12
(58) Field of Search ............................ 424/45, 46, 489; 514/2, 12, 948

(56) References Cited

U.S. PATENT DOCUMENTS 5,578,567 A    11/1996   Cardinaux et al. ............ 514/12

FOREIGN PATENT DOCUMENTS

| EP | 0 490 806 | 6/1992 |
|---|---|---|
| GB | 2 248 550 | 4/1992 |
| GB | 2 268 185 | 1/1994 |
| JP | 60-224616 | 11/1985 |
| JP | 63-115821 | 5/1988 |

*Primary Examiner*—Jose' G. Dees
*Assistant Examiner*—Konata M. George
(74) *Attorney, Agent, or Firm*—Crowell & Moring LLP

(57) ABSTRACT

A nasally administrable composition of a physiologically active substance, wherein an effective amount of said physiologically active substance is dispersed homogeneously in and adsorbed homogeneously onto a fine powdery form of a cereal, thereby enhancing the absorption of the physiologically active substance into a body via the nasal route. Examples of the cereal are rice, wheat, soybean, corn, foxtail, millet, buckwheat and the like, especially rice, and the physiologically active substance is a physiologically active peptide.

19 Claims, 3 Drawing Sheets

Figure 1  Carrier: Fine powdery form of Akita-komachi

Figure 2  Carrier: Calcium carbonate

NASALLY ADMINISTRABLE COMPOSITIONS

TECHNICAL FIELD

The present invention relates to a nasally administrable composition and more particularly, a nasally administrable composition that provides excellent absorption of a physiologically active substance into human bodies through nasal administration.

BACKGROUND ART

Various physiologically active substances, including calcitonin, insulin, parathyroid hormone (PTH), human grows hormone (HGH), interferon, and the like and their derivatives, are macromolecular compound used for various medical purposes in clinical practice owing to their unique physiological activities.

These physiologically active substances, however, can little be absorbed intact from the mucous membrane of the intestine because they are likely to be decomposed with proteases existing in the digestive tract or are high in molecular weight and polarity. Hence, they are hard to administer orally and their administration route is limited to injection.

Recently, there has been proposed nasally administrable preparations of these physiologically active substances instead of injection route. By the nasally administration, the physiologically active substances are absorbed through the mucous membrane of the nasal cavity into the body, and the bioavailability thereof is enhanced to similar level as that obtained with conventional injectable preparations. Therefore, the nasally administrable preparations are expected to be useful preparations for administration of physiologically active substances.

The physiologically active substances to be absorbed into the human body through nasal administration are not limited to those mentioned above, and other physiologically active substances conventionally administered in oral or injectable preparations are also applicable for nasally administration. Accordingly, there has been demand for development of more effective nasally administrable preparations for these physiologically active substances.

Previously, the inventor developed a nasally administrable composition to nasally administer physiologically active substances unlikely to be orally administered or other physiologically active substances with higher absorbability and less irritation, and he found that a nasally administrable composition wherein physiologically active substance is dispersed homogeneously in and adsorbed onto several specific carriers.

The present inventor further performed investigations to develop the nasally administrable compositions, and he perceived a fine powdery form of cereal such as rice, wheat, soybean, corn, foxtail, millet, buckwheat and the like, which has not yet been studied as a carrier for use with nasally administrable composition. That is, when physiologically active substances were administered nasally with fine powdery form of cereal as a carrier, those active substances were extremely well absorbed, and their absorbability was equivalent to or even higher than that obtained by other nasally administrable preparations so far proposed, and the pharmaceutical stability of the compositions were excellent. Thus the present inventor completed the invention based on these findings.

DISCLOSURE OF THE INVENTION

Accordingly, the object of the present invention is to provide a new nasally administrable composition that can nasally administer physiologically active substances with higher bioavailability though the mucous membrane of nasal cavity, and with the excellent pharmaceutical stability of the compositions.

One aspect of the present invention is to provide the nasally administrable composition containing a physiologically active substance and fine powdery form of cereal, wherein a physiologically effective amount of said physiologically active substance is dispersed homogeneously in and adsorbed homogeneously onto said fine powdery form of cereal.

The other aspect of the present invention is to provide fine powdery form of cereal as a carrier to be used for nasally administrable composition.

In still another aspect of the present invention, use of fine powdery form of cereal as a carrier for nasally administrable composition, is provided.

The nasally administrable composition of the present invention constitutes a characteristic future of using fine powdery form of cereal as a carrier to be used for nasally administrable composition, which has not yet been. Therefore, according to the present invention, when the physiologically active substance was administered nasally with fine powdery form of cereal as the carrier, the active substance contained in the composition may be extremely well absorbed into the body through the mucous membrane of the nasal cavity.

BEST MODES FOR CARRYING OUT THE INVENTION

Figure 1:
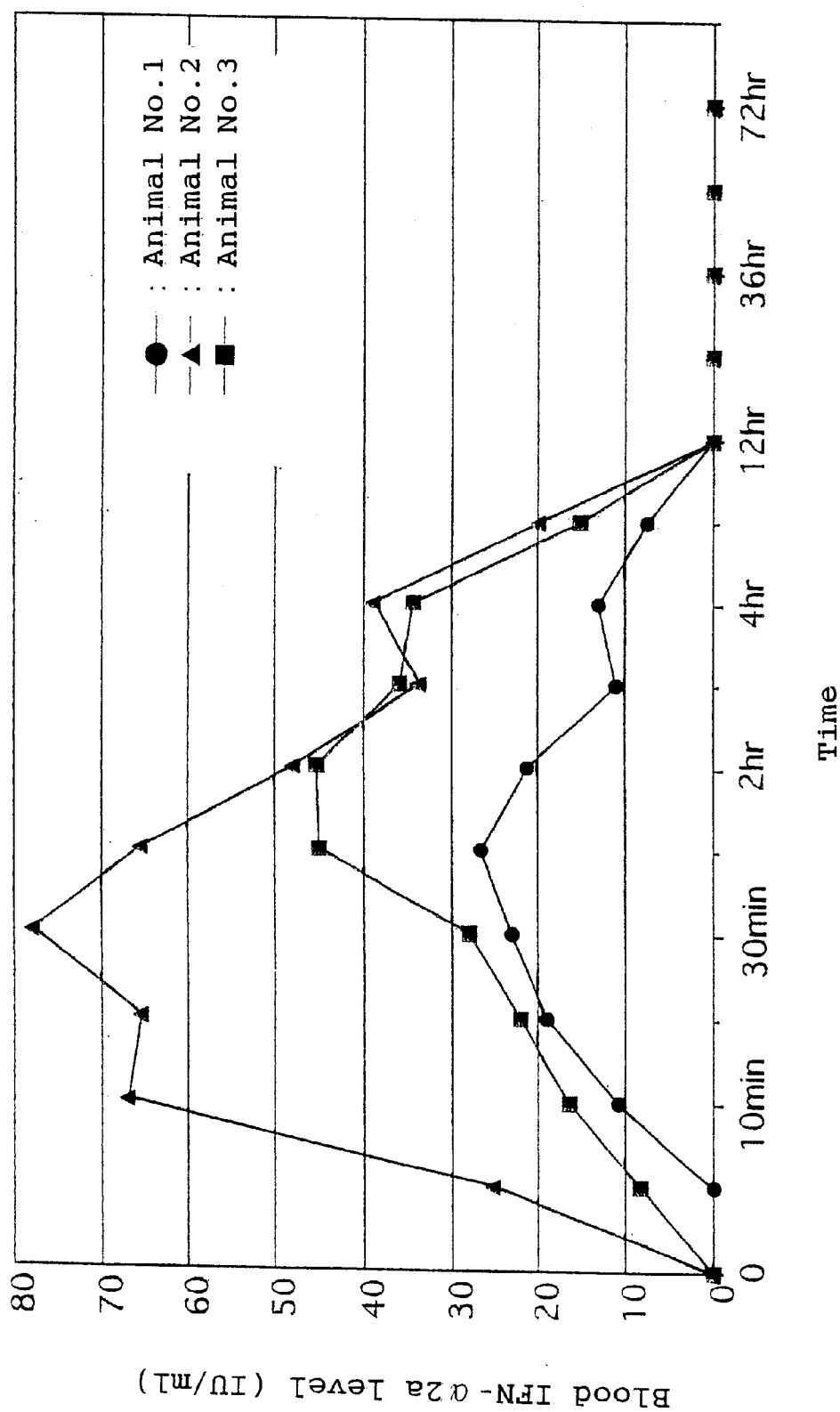
FIG. 1 is a graph showing a change of blood INF-α2a level with time passage after administration of the composition of the present invention in the pharmacological test example 1.
Figure 2:
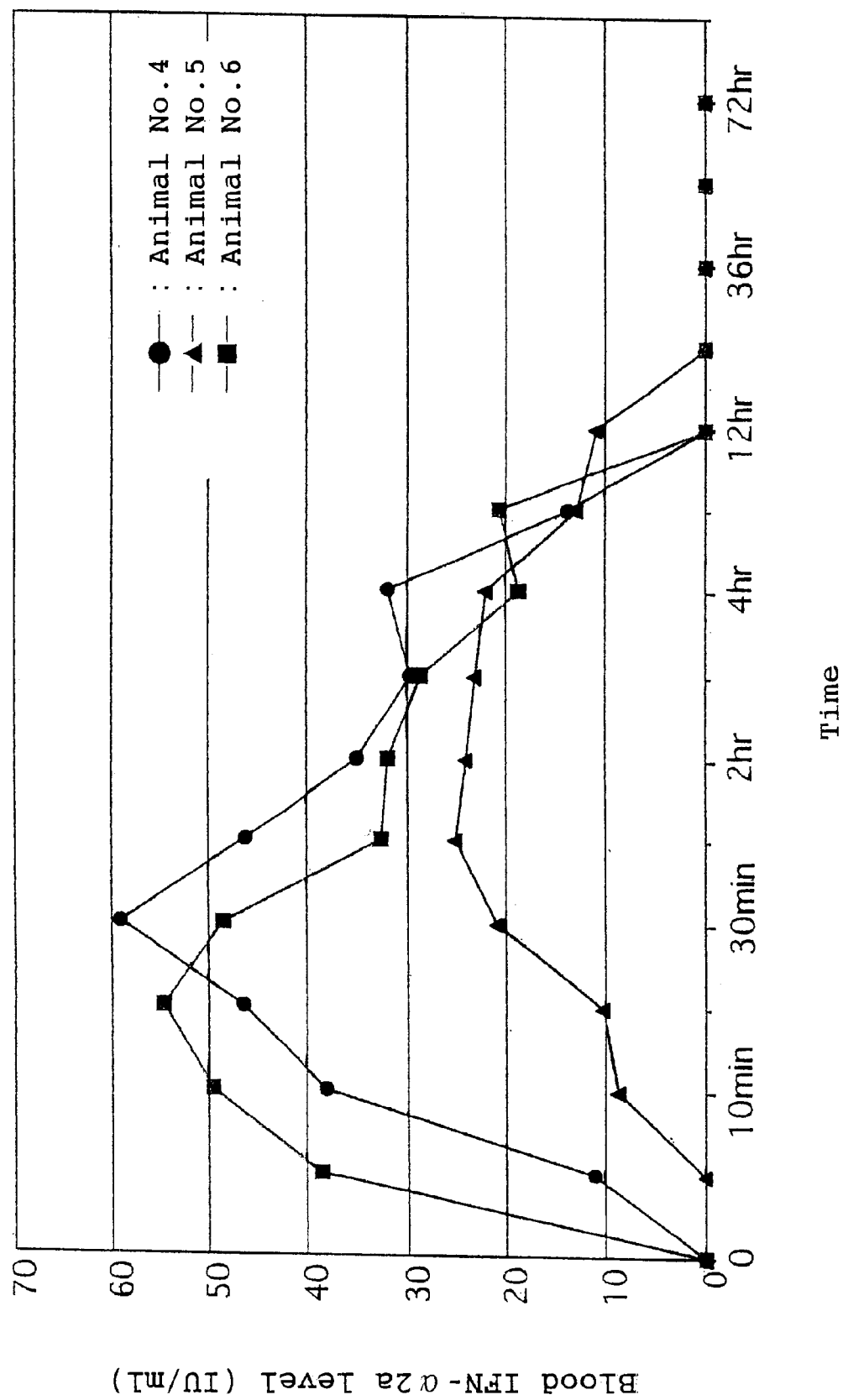
FIG. 2 is a graph showing a change of blood INF-α2a level with time passage after administration of the reference composition in the pharmacological test example 1.
Figure 3:
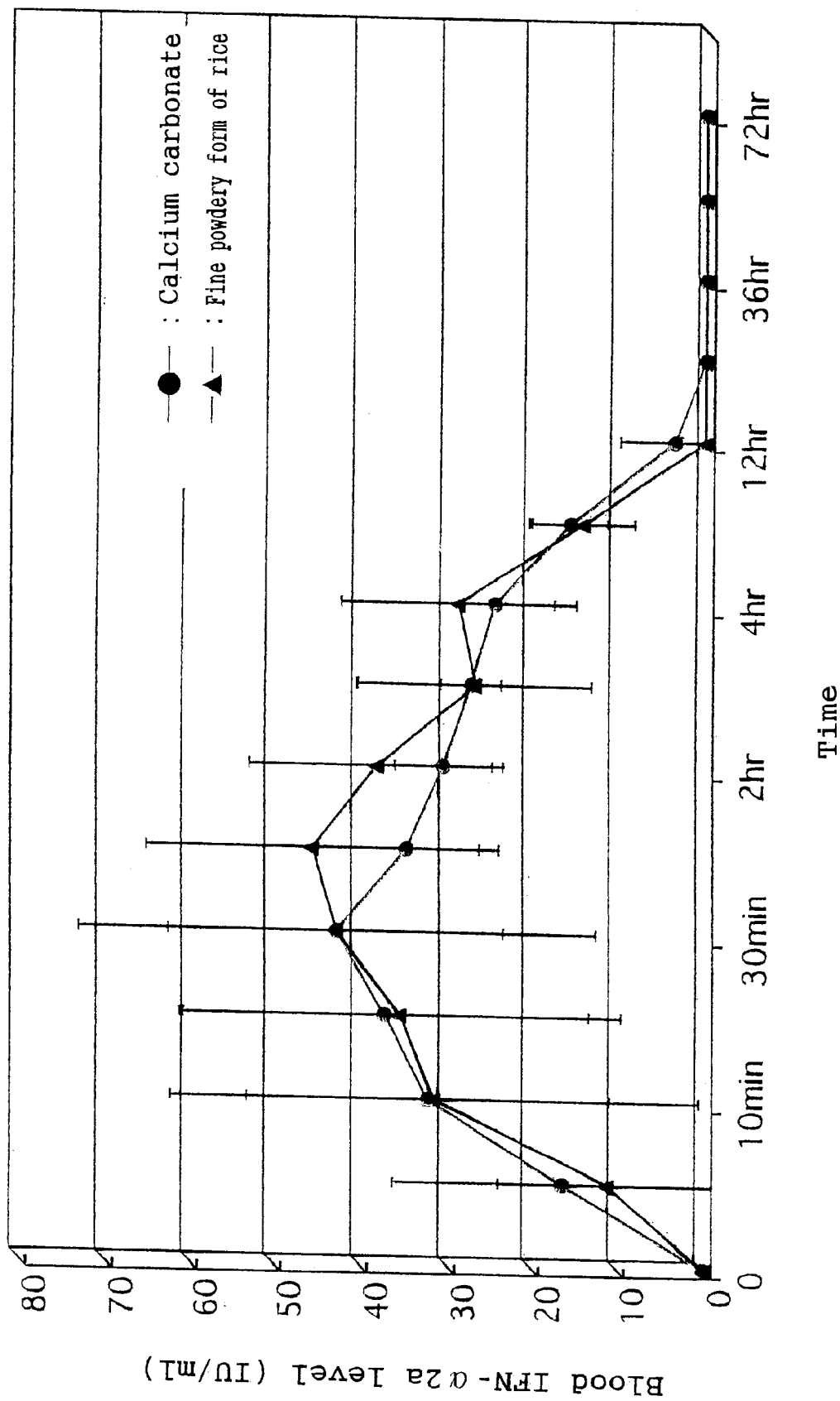
FIG. 3 is a graph showing the comparison of change in mean blood INF-α2a concentration level with time passage after administration of the composition of the present invention and reference composition in the pharmacological test example 1.

The fine powdery form of cereal to be used in the present invention as a carrier may have a mean particle size from about 10 $\mu$m to about 500 $\mu$m, preferably from about 15 $\mu$m to 300 $\mu$m, since the physiologically active substance has to be atomized to the nasal cavity with the carrier.

The cereal to be used as a carrier of the present invention may be, for example, rice, wheat, soybean, corn, foxtail, millet, buckwheat and the like, which is eaten by the human beings as a staple principal food. Among them, the purified starch component of wheat or corn, that is corn starch, has been commonly used in the drugs as the excipients; however, the fine powdery form of these cereals intact has never been used as a carrier for the nasally administrable compositions up to present, and is first attempt by the present inventor.

The fine powdery form of the cereal, such as rice, may be prepared by pulverizing the polished rice by conventional technique, in order to obtain the purposed fine powdery form having a suitable mean particle size. The rice to be used for the present invention may include Japanese and foreign rice; however, Japanese rice is preferred. The examples of such Japanese rice are sold in Japanese brand name "Akita-komachi", "Sasa-nishiki", "Koshi-hikari", "Hitome-bore" and so on.

The fine powdery form of other cereal may also be foreign as well as Japanese cereal prepared by pulverizing in conventional technique, in order to obtain the fine powdery form having a suitable mean particle size.

The physiologically active substances to be contained in the nasally administrable composition of the present invention are not particularly limited as long as it is nasally administrable. The substances unlikely to be orally administered, especially, physiologically active peptides, can be used. The inventor of the present invention had found that the physiologically active peptides, such as glycoproteins, peptide hormones, physiologically active proteins and enzyme proteins show high absorption rate into the body.

Glycoproteins as the physiologically active substance include various interferons, such as $\alpha$-interferon, $\beta$-interferon, $\gamma$-interferon and the like.

Peptide hormones include calcitonin, insulin, thyrotropin-releasing hormone (TRH) such as thyroliberin, luteinizing hormone-releasing hormone (LH-RH) such as buserelin and leuprolelin, LH-RH antagonists, somatostatin (growth hormone-releasing factor), adrenocorticotropic hormone (ACTH), adrenocorticotropic hormone-releasing hormone (CRH) such as corticoliberin, growth hormone-releasing hormone (GH-RH) such as somatorelin and the like.

Furthermore, they include gonadotropin (gonadotropic hormone), gonadotropin-releasing hormone (GnRH) such as gonadoliberin, parathyroid hormone (PTH), thyroid-stimulating hormone (TSH), growth hormone such as somatotropin, prolactin (mammotropic hormone), follicle-stimulating hormone (FSH), glucagon, vasopressin, parathormone (parathyroid hormone), angiotensin, gastrin, secretin, melanocyte-stimulating hormone, oxytocin, protirelin, corticotropin, thyrotropin (thyroid-stimulating hormone), opioid peptide such as $\beta$-endorphin and enkephalin, G-CSF, erythropoietin, superoxide dismutase (SOD) and the like.

In addition, various types of interleukins, urokinase, lysozymes, and vaccines are also included.

Physiologically active peptides of the present invention are not limited to those mentioned above, and other peptides which can be combined with the specific carrier and administered nasally may also be used to make the compositions of the present invention.

Furthermore, the physiologically active substances unlikely to be administered orally can be used in the nasally administrable composition of the present invention. Such physiologically active substances may include various kinds of drugs on the market, or those under clinical development. Examples of such physiologically active substances include hypnotic and sedatives, anti-epileptics, minor tranquilizers, major tranquilizers, antidepressants, muscle relaxants, anti-allergic agents, antirheumatics, cardiotonics, antiarrthymics, antihypertensive diuretics, $\alpha$-blocking agents, $\beta$-blocking agents, calcium channel antagonists, angiotensin converting enzyme inhibitors (AEC), antihypertensives, vitamins, coronary vasodilators, cerebral circulation and metabolism ameliorators, anti-arteriosclerotcs, cardiovascular agents, bronchodilators, anti-ucceratives, antiemetics, antiobesity agents, platelet aggregation inhibitors, antidiabetics/symptomatic antidiabetics, DNA/RNA, and so on.

The amount of the above-mentioned physiologically active substances to be contained in the composition of the present invention is not specifically limited and may contain at least effective amounts of the active substances. Thus, it is preferred for the physiologically active substance mentioned above to be contained at a rate from 0.0001 to 30 weight %, preferably from 0.01 to 20 weight %, more preferably from 0.1 to 5.0 weight %, per 100% total weight of the composition.

Furthermore, the amount of the fine powdery form of the cereal as the carrier may be 70 to 99.995 weight %, preferably 80 to 99.99 weight %, and more preferably 95 to 99.9 weight %, per 100% total weight of the composition.

The composition of the present invention is prepared by admixing the physiologically active substance with the fine powdery form of the cereal as a specific carrier, thereby yielding a fine powder of a nasally administrable composition in which the physiologically active substance is dispersed homogeneously in and adsorbed homogeneously onto the carrier.

The composition thus prepared can be administered alone or with other pharmaceutically known ingredients added as desired.

In order to prevent the activity loss of the physiologically active substance prior to administration such as nasal administration, it may be filled in low-grease type capsules and packaged in an appropriate form, preferably in a closed form such as combined blister and aluminum packaging.

The specific effects offered by the pharmaceutical composition for nasal administration according to the present invention are shown below by way of Test Examples.

PHARMACOLOGICAL TEST EXAMPLE 1

Absorption After Nasal Administration in Cynomolgus Monkey

Interferon-$\alpha$2a (IFN-$\alpha$2a), a glycoprotein, was selected as a physiologically active substance, and a fine powdery form of "Akita-komachi", Japanese rice, was selected as the carrier to prepare the nasally administrable composition of the present invention. The mean particle size of the carrier was 60 $\mu$m.

The single administration amount of IFN-$\alpha$2a is adjusted to be 36,000 units/body weight.

The composition was nasally administered to three cynomolgus monkeys weighing approximately 3 kg, and a blood sample was taken before administration and at 5, 10, 15, 30, 60, 120, 180, 240 and 360 minutes, and 12, 24, 48 and 72 hours after administration to determine the blood INF-$\alpha$2a level.

As the comparative composition, calcium carbonate which was previously proposed by the present inventor, having a mean particle size of 100 $\mu$m, was used as the carrier and IFN-α2a in the single administration amount of 36,000 units/body weight was administered nasally, then a blood sample was taken in same manner to determine the blood INF-α2a level.

TABLE 1

Blood IFN-α2a level after nasal administration in cynomolgus monkey
Blood IFN-α2a level (IU/ml)

| Carrier Time | Fine powdery form of rice (Akita-komachi) Mean particle size: 60 μm Animal No. | | | Calcium carbonate Mean particle size: 100 μm Animal No. | | |
|---|---|---|---|---|---|---|
| (min.) | No. 1 | No. 2 | No. 3 | No. 4 | No. 5 | No. 6 |
| 0 | ~6 | ~6 | ~6 | ~6 | ~6 | ~6 |
| 5 | 6 | 25.0 | 8.4 | 11.1 | 6 | 38.5 |
| 10 | 10.9 | 66.9 | 16.5 | 38.1 | 8.6 | 49.6 |
| 15 | 19.0 | 65.3 | 22.0 | 46.5 | 10.1 | 54.7 |
| 30 | 23.0 | 77.6 | 27.8 | 59.1 | 20.9 | 48.6 |
| 60 | 26.5 | 65.3 | 45.0 | 46.2 | 25.1 | 32.5 |
| 120 | 21.2 | 47.9 | 45.3 | 35.1 | 24.0 | 31.8 |
| 180 | 11.2 | 33.4 | 35.6 | 29.7 | 23.0 | 28.5 |
| 240 | 13.1 | 38.7 | 34.1 | 31.8 | 22.0 | 18.7 |
| 360 | 7.7 | 19.8 | 15.1 | 13.7 | 12.9 | 20.6 |
| 12hours | ~6 | ~6 | ~6 | ~6 | 10.9 | ~6 |
| 24hours | ~6 | ~6 | ~6 | ~6 | ~6 | ~6 |

As apparent from Table 1 above, the composition of the present invention using a fine powdery form of rice (Akita-komachi) as the carrier attained a high degree of absorption of INF-α2a into the body via the nasal route. Furthermore, the bioavailability of the present invention's composition is equal to that of the comparative composition using calcium carbonate known to possess relatively fine bioavailability as the carrier of nasal administration.

The changes of blood INF-α2a level with time passage are shown in FIG. 1 (carrier: fine powdery form of rice) and FIG. 2 (carrier: calcium carbonate), and the changes of mean blood INF-α2a concentration level compared in time passage after administration of the composition of the present invention and comparative composition are shown in FIG. 3.

PHARMACOLOGICAL TEST EXAMPLE 2

Absorption After Nasal Administration in Dog

Interferon-α2a (IFN-α2a), a glycoprotein, was selected as a physiologically active substance as in test example 1, and a fine powdery form of "Akita-komachi", Japanese rice, was selected as the carrier to prepare the nasally administrable composition of the present invention. The mean particle size of the carrier was 60 μm.

The single administration amount of IFN-α2a is adjusted to be 36,000 units/body weight.

The composition was nasally administered to three beagle dogs weighing approximately 5 kg, and a blood sample was collected before administration, and at 5, 10, 15, 30, 60, 120, 180, 240 and 360 minutes, and 12, 24, 48 and 72 hours after administration to determine the blood INF-α2a level.

As the comparative composition, calcium carbonate which was previously proposed by the present inventor, having a mean particle size of 100 μm, was used as the carrier and IFN-μ2a in the single administration amount of 36,000 units/body weight was administered nasally, then a blood sample was taken in the same manner to determine the blood INF-α2a level.

TABLE 2

Blood IFN-α2a level after nasal administration in dog
Blood IFN-α2a level (IU/ml)
Carrier: Fine powdery form of Akita-komachi
Mean particle size: 60 μm

| Time (Minutes) | Animal No. No. 1 | No. 2 | No. 3 | Mean | SD |
|---|---|---|---|---|---|
| 0 | 0.0 | 0.0 | 0.0 | 0.0 | 0.0 |
| 5 | 0.0 | 25.0 | 8.4 | 11.1 | 12.7 |
| 10 | 10.9 | 66.9 | 16.5 | 31.4 | 30.8 |
| 15 | 19.0 | 65.3 | 22.0 | 35.4 | 25.9 |
| 30 | 23.0 | 77.6 | 27.8 | 42.8 | 30.2 |
| 60 | 26.5 | 65.3 | 45.0 | 45.6 | 19.4 |
| 120 | 21.2 | 47.9 | 45.3 | 38.1 | 14.7 |
| 180 | 11.2 | 33.4 | 35.6 | 26.7 | 13.5 |
| 240 | 13.1 | 38.7 | 34.1 | 28.6 | 13.6 |
| 360 | 7.7 | 19.8 | 15.1 | 14.2 | 6.1 |
| 12hours | 0.0 | 0.0 | 0.0 | 0.0 | 0.0 |
| 24hours | 0.0 | 0.0 | 0.0 | 0.0 | 0.0 |

TABLE 3

Blood IFN-α2a level after nasally administration in dog
Blood IFN-α2a level (IU/ml)
Carrier: Calcium carbonate
Mean particle size: 100 μm

| Time (Minutes) | Animal No. No. 1 | No. 2 | No. 3 | Mean | SD |
|---|---|---|---|---|---|
| 0 | 0.0 | 0.0 | 0.0 | 0.0 | 0.0 |
| 5 | 11.1 | 0.0 | 38.5 | 16.5 | 19.8 |
| 10 | 38.1 | 8.6 | 49.6 | 32.1 | 21.1 |
| 15 | 46.5 | 10.1 | 54.7 | 37.1 | 23.7 |
| 30 | 59.1 | 20.9 | 48.6 | 42.9 | 19.7 |
| 60 | 46.2 | 25.1 | 32.5 | 34.6 | 10.7 |
| 120 | 35.1 | 24.0 | 31.8 | 30.3 | 5.7 |
| 180 | 29.7 | 23.0 | 28.5 | 27.1 | 3.6 |
| 240 | 31.8 | 22.0 | 18.7 | 24.2 | 6.8 |
| 360 | 13.7 | 12.9 | 20.6 | 15.7 | 4.2 |
| 12hours | 0.0 | 10.9 | 0.0 | 3.6 | 6.3 |
| 24hours | 0.0 | 0.0 | 0.0 | 0.0 | 0.0 |

As is apparent from Table 2 and 3 above, the composition of the present invention using a fine powdery form of rice (Akita-komachi) as the carrier also attained a high degree of absorption of INF-α2a into the body via the nasal route in the case of the dog. Furthermore, the bioavailability of the present invention's composition is equal to that of the comparative composition using calcium carbonate known to possess relatively fine bioavailability as the carrier of nasal administration.

The biologically active substances other than interferon can be absorbed into the body by the composition of the present invention. Further, a high degree of bioavailability of the composition can also be obtained using a fine powdery form of rice other than Akita-komachi, such as Koshi-hikari, Sasa-nishiki and Hitome-bore as the carrier.

Furthermore, by using a fine powdery form of other cereals such as buckwheat as the carrier for the composition of the present invention, a high degree of bioavailability of the physiologically active substances can also be obtained.

The following are formulation examples of the composition according to the present invention, which, however, are non-limiting. Formulation Example 1: calcitonin composition A calcitonin composition was prepared from the following components:

| | |
|---|---|
| Calcitonin | 6,540 IU |
| Fine powdery form of rice (Akita-komachi) | the balance |
| Total | 1,000 mg |

FORMULATION EXAMPLE 2

Interferon-α2a Composition

An interferon-α2a composition was prepared from the following components:

| | |
|---|---|
| Interferon-α 2a | 10,000 MIU |
| Fine powdery form of rice (Akita-komachi) | the balance |
| Total | 500 mg |

Industrial Applicability

The composition of the present invention wherein physiologically active peptides, including calcitonin, insulin, IFN and the like are dispersed homogeneously in and adsorbed homogeneously onto the fine powdery form of cereal, especially, the fine powdery form of rice which has not yet been studied as a carrier for nasally administrable composition, can be administered via nasal route, thereby enhancing the absorption of such peptides through mucous membrane of the nasal cavity into the body. Thus the present invention can provide considerable benefits for clinical therapy.

What is claimed is:

1. A nasally administrable composition, comprising an effective amount of a physiologically active substance dispersed homogeneously in and adsorbed homogeneously onto a fine powdery form of a cereal.

2. The nasally administrable composition as claimed in claim 1, wherein said cereal is selected from the group consisting of rice, wheat, soybean, corn, foxtail, millet and buckwheat.

3. The nasally administrable composition as claimed in claim 1 or 2, wherein said physiologically active substance is a nasally administrable physiologically active substance.

4. The nasally administrable composition as claimed in claim 1 or 2, wherein said physiologically active substance is a physiologically active selected from the group consisting of glycoproteins, peptide hormones, physiologically active proteins and enzyme proteins.

5. The nasally administrable composition as claimed in claim 1 or 2, wherein said physiologically active substance is interferon.

6. The nasally administrable composition as claimed in claim 1 or 2, wherein a mean particle size of said fine powdery form of cereal ranges from 10 µm to 500 µm.

7. A fine powdery form of a cereal as a carrier in a nasally administrable composition containing a physiologically active substance.

8. The fine powdery form of cereal as claimed in claim 7, wherein said cereal is selected from the group consisting of rice, wheat, soybean, corn, foxtail, millet and buckwheat.

9. The fine powdery f or m of cereal as claimed in claim 7 or 8, wherein said physiologically active substance is a nasally administrable physiologically active substance.

10. The fine powdery form of cereal as claimed in claim 7 or 8, wherein said physiologically active substance is a physiologically active selected from the group consisting of glycoproteins, peptide hormones, physiologically active proteins and enzyme proteins.

11. The fine powdery form of cereal as claimed in claim 7 or 8, wherein said physiologically active substance is interferon.

12. The fine powdery form of cereal as claimed in claim 7 or 8, wherein a mean particle size of said fine powdery form of cereal ranges from 10 µm to 500 µm.

13. A method for administering a physiologically active substance to a mammal comprising nasally administering an effective amount of said physiologically active substance dispersed homogeneously in and adsorbed homogeneously onto a fine powdery form of a cereal.

14. The method as claimed in claim 13, wherein said cereal is selected from the group consisting of rice, wheat, soybean, corn, foxtail, millet and buckwheat.

15. The method as claimed in claim 13 or 14, wherein said physiologically active substance is a nasally administrable physiologically active substance.

16. The method as claimed in claim 13 or 14, wherein said physiologically active substance is a physiologically active selected from the group consisting of glycoproteins, peptide hormones, physiologically active proteins and enzyme proteins.

17. The method as claimed in claim 13 or 14, wherein said physiologically active substance is interferon.

18. The method as claimed in claim 13 or 14, wherein a mean particle size of said fine powdery form of cereal ranges from 10 µm to 500 µm.

19. A kit comprising packaging material and a physiologically active substance dispersed homogeneously in and adsorbed homogeneously onto a fine powdery form of a cereal contained within said packaging material, and wherein said packaging material comprises a package insert or a label which provides directions for practicing the method claimed in claim 13 or 14.

* * * * *